United States Patent
Sugimoto

(10) Patent No.: US 9,709,490 B2
(45) Date of Patent: Jul. 18, 2017

(54) REFRACTIVE INDEX DISTRIBUTION MEASURING METHOD, REFRACTIVE INDEX DISTRIBUTION MEASURING APPARATUS, AND OPTICAL ELEMENT MANUFACTURING METHOD

(71) Applicant: CANON KABUSHIKI KAISHA, Tokyo (JP)

(72) Inventor: Tomohiro Sugimoto, Yoshikawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 48 days.

(21) Appl. No.: 14/959,878

(22) Filed: Dec. 4, 2015

(65) Prior Publication Data
US 2016/0161403 A1   Jun. 9, 2016

(30) Foreign Application Priority Data

Dec. 8, 2014 (JP) .................. 2014-248475
Sep. 28, 2015 (JP) .................. 2015-190070

(51) Int. Cl.
*G01N 21/41* (2006.01)
*G01N 21/45* (2006.01)
*G01M 11/02* (2006.01)
*G01N 21/958* (2006.01)

(52) U.S. Cl.
CPC .......... *G01N 21/45* (2013.01); *G01M 11/0214* (2013.01); *G01M 11/0228* (2013.01); *G01N 21/958* (2013.01)

(58) Field of Classification Search
CPC ........ G01N 21/41; G01N 21/45; G01M 11/00
See application file for complete search history.

(56) References Cited

FOREIGN PATENT DOCUMENTS

JP         2014-196966 A    10/2014

*Primary Examiner* — Kara E Geisel
*Assistant Examiner* — Maurice Smith
(74) *Attorney, Agent, or Firm* — Canon USA Inc., IP Division

(57) ABSTRACT

A test unit is formed by sandwiching a test lens by a first reference lens whose shape and refractive index are known, a second reference lens whose shape and refractive index are known, and a medium. A wavefront of light transmitted through the test unit is measured, and, by using the shape and the refractive index of the first reference lens, the shape and refractive index of the second reference lens, and the measured wavefront of the test unit, the refractive index distribution of the test lens is calculated.

13 Claims, 7 Drawing Sheets

REFRACTIVE INDEX DISTRIBUTION MEASURING METHOD, REFRACTIVE INDEX DISTRIBUTION MEASURING APPARATUS, AND OPTICAL ELEMENT MANUFACTURING METHOD

BACKGROUND OF THE INVENTION

Field of the Invention

The present invention relates to a refractive index distribution measuring method and a refractive index distribution measuring apparatus for measuring a refractive index distribution of an optical element.

Description of the Related Art

In a method for manufacturing a lens by molding, three physical quantities including the shape, the refractive index, and the refractive index distribution deviate from design values. In particular, defects in the refractive index distribution that occurs in the interior of the lens adversely affect optical performance. Therefore, in manufacturing a lens by molding, a technique for nondestructively measuring the refractive index distribution of the molded lens under the condition that the shape and the refractive index differ from the design values is required.

In a measuring method disclosed in Japanese Patent Application Laid-Open No. 2014-196966, a measurement cell in which a test object is sandwiched by a first reference element and a second reference element and in which a gap between the test object and the first reference element and a gap between the test object and the second reference element are filled with matching oil is formed. The refractive indices of the first and second reference elements are assumed to be substantially the same as the refractive index of the test object. Herein "substantially the same" means that values are within a negligible difference. Therefore, for the refractive indices of the first and second reference elements to be substantially the same as that of the test object, differences in optical performance of the test object would be negligible as compared to the optical performance of the first and second reference elements. The surface shapes of the first and second reference elements are the reverse of the surface shape of the test object. Then, interference fringes of the measurement cell are measured, phase distribution data is calculated from the interference fringes, and the difference between the phase distribution data and previously set reference data is calculated, to determine the refractive index distribution of the test object.

In the measuring method disclosed in Japanese Patent Application Laid-Open No. 2014-196966, by using the matching oil and the reference elements whose refractive indices are assumed to be substantially the same as the refractive index of the test object, the influences of refraction by the test object are cancelled to determine the refractive index distribution of the test object. However, in the method for manufacturing a lens by molding, differences occur among the refractive index of the test object, the refractive indices of the reference elements, and the refractive index of the matching oil because not only the shape of the test object but also the refractive index of the test object deviates from the design value for different molding conditions.

Due to the differences in the refractive indices, the influences of refraction by the test object cannot be completely cancelled. Therefore, an error in the shape of the test object (deviation from the design value of the shape) occurs as an error in the refractive index distribution. Further, just the difference between the refractive index of the test object and the refractive indices of the reference elements also causes an error in the calculation of the refractive index distribution. Therefore, in order to determine the refractive index distribution with high precision, a computation for correcting the influences of the error in the shape of the test object and the error in the refractive index of the test object (deviation from the design value of the refractive index) is required.

The present invention provides, for example, a refractive index distribution measuring method and a refractive index distribution measuring apparatus for allowing the refractive index distribution of a lens to be nondestructively measured with high precision.

SUMMARY OF THE INVENTION

According to an aspect of the present invention, a refractive index distribution measuring method includes a step of measuring a wavefront transmitted through a test unit that is formed by sandwiching a test lens by a first reference lens whose shape and refractive index are known, a second reference lens whose shape and refractive index are known, and a medium; and a step of calculating a refractive index distribution of the test lens by using the shape and the refractive index of the first reference lens, the shape and the refractive index of the second reference lens, and the measured wavefront of the test unit.

A lens manufacturing method including the step of molding a lens and the step of evaluating optical characteristics of the molded lens by measuring the refractive index distribution of the lens by using the above-described refractive index distribution measuring method is also another aspect of the present invention.

According to still another aspect of the present invention, there is provided a refractive index distribution measuring apparatus including a measuring unit configured to measure a transmitted wavefront of a test unit that is formed by sandwiching a test lens by a first reference lens whose shape and refractive index are known, a second reference lens whose shape and refractive index are known, and a medium; and a calculating unit configured to calculate a refractive index distribution of the test lens by using the shape and the refractive index of the first reference lens, the shape and the refractive index of the second reference lens, and the transmitted wavefront of the test unit.

Further features of the present invention will become apparent from the following description of exemplary embodiments with reference to the attached drawings.

DESCRIPTION OF THE EMBODIMENTS

Embodiments of the present invention are hereunder described with reference to the drawings.

First Embodiment

Figure 1:
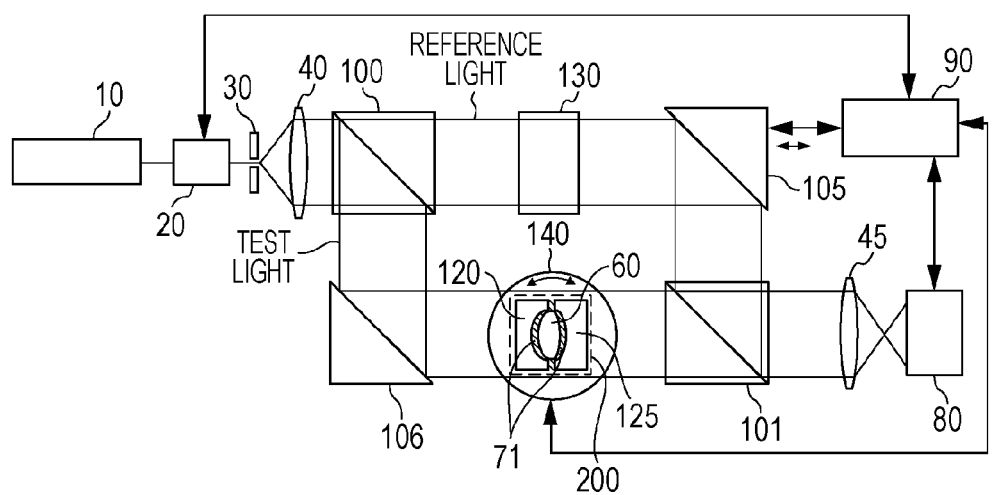
FIG. 1 is a schematic view of a structure of a refractive index distribution measuring apparatus according to a first embodiment of the present invention.

FIG. 1 is a schematic view of a structure of a refractive index distribution measuring apparatus according to a first embodiment of the present invention. The refractive index distribution measuring apparatus according to the first embodiment is formed on the basis of a Mach-Zehnder interferometer. The measuring apparatus includes a light source 10, an interference optical system, a test unit 200, a compensating plate 130, a detector 80, and a computer 90. The measuring apparatus measures the refractive index distribution of a test lens 60. In the embodiment, the test lens is a lens having a positive refractive power. However, as long as a refractive optical element is used, it is possible to measure the refractive index distribution regardless of whether the refractive power is positive or negative.

The light source 10 is a light source that is capable of emitting light having a plurality of wavelengths (such as a super continuum light source). The light having a plurality of wavelengths becomes quasi-monochromatic light after passing through a monochromator 20. The quasi-monochromatic light passes through a pinhole 30 and becomes a divergent wave, and passes through a collimator lens 40 and becomes parallel light.

The interference optical system includes beam splitters 100 and 101, and mirrors 105 and 106. The interference optical system splits the light that has passed through the collimator lens 40 into reference light that does not pass through the test lens 60 and test light that passes through the test lens 60, and causes the reference light and the test light to interfere with each other and the interference light to be guided to the detector 80.

The test unit 200 includes the test lens 60, a first reference lens 120, a second reference lens 125, and a medium 71. The first reference lens 120, the medium 71, the test lens 60, the medium 71, and the second reference lens 125 are disposed side by side in this order.

At a particular wavelength, the refractive index of the first reference lens 120 is equal to the refractive index of the test lens 60. Since the test lens 60 has a refractive index distribution, the phrase "the refractive index of the test lens 60" refers to the refractive index at a particular point within the test lens 60. The particular point may be any point in interior of the test lens 60.

The second reference lens 125 is formed of the same material as the first reference lens 120. The refractive index of the medium 71 need not be equal to the refractive index of the test lens 60 (for example, when a refractive index $n_d$ of the test lens 60 is approximately 1.9, a refractive index $n_d$ of the medium 71 may be approximately 1.7). The closer the refractive index of the medium is to the refractive index of the test lens 60, the better. This is because the influences of refraction at a surface of the test lens 60 can be reduced. However, the medium may be air.

The first reference lens 120 has a planar shape and a shape that is substantially the same as the shape of the first surface of the test lens 60. The second reference lens 125 has a shape that is substantially the same as the shape of the second surface of the test lens 60 and a planar shape. That is, a surface of the first reference lens 120 and a surface of the second reference lens 125 that are on the opposite side to the test lens 60 are planar surfaces.

In the first embodiment, "substantially the same surface shapes" refers to surfaces whose shapes match within a range on the order of manufacturing errors of the surface shape of the test lens. The surface shape and the refractive index of the first reference lens 120, and the surface shape and the refractive index of the second reference lens 125 are known. The first reference lens 120 and the second reference lens 125 are manufactured by, for example, grinding/polishing so that their refractive index distributions can be negligible. The test unit 200 is disposed on a rotating stage 140 having a rotating shaft in a vertical direction with respect to incident test light.

The test light reflected by the beam splitter 100 is reflected by the mirror 106 and passes through the test unit 200. On the other hand, the reference light that has passed through the beam splitter 100 passes through the compensating plate 130 and is reflected by the mirror 105. The compensating plate 130 is a glass block for reducing the difference between the length of an optical path of the test light and the length of an optical path of the reference light. If a coherence length of the light that has passed through the monochromator 20 is long, the compensating plate 130 is not required. The reference light and the test light are combined by the beam splitter 101 to form interference light.

The refractive index of the medium 71 is calculated by measuring the air temperature near the medium 71 by using a thermometer (not shown) and converting to the refractive index on the basis of the measured temperature. However, in the first embodiment, it is not necessary to calculate the refractive index of the medium 71.

The mirror 105 is driven in the directions of a double-headed arrow in FIG. 1 by a driving mechanism (not shown). The driving directions are not limited to the directions of the double-headed arrow in FIG. 1. The mirror 105 may be driven in any direction as long as the difference between the length of the optical path of the reference light and the length of the optical path of the test light is changed by driving the mirror 105. The driving mechanism of the mirror 105 is composed of, for example, a piezo stage. The driving amount of the mirror 105 is measured by a length measuring unit (such as a laser displacement measuring apparatus or an encoder)(not shown), and is controlled by the computer 90. The difference between the length of the optical path of the reference light and the length of the optical path of the test light is adjusted by the driving mechanism of the mirror 105.

The interference light formed by the beam splitter 101 is detected by the detector 80 (such as a CCD or a MOS) via an imaging lens 45. An interference signal detected by the detector 80 is sent to the computer 90. The detector 80 is disposed at a position conjugate with the test lens 60 with respect to the imaging lens 45. That is, interference fringes and an image at the test lens 60 are formed on the detector 80.

The computer 90 includes a calculating unit and a controller. The calculating unit calculates the refractive index distribution of the test lens on the basis of detection results of the detector 80. The controller controls the wavelength of light that passes through the monochromator 20, the driving amount of the mirror 105, and the amount of rotation of the rotating stage 140. The computer 90 is composed of, for example, a CPU.

Figure 2:
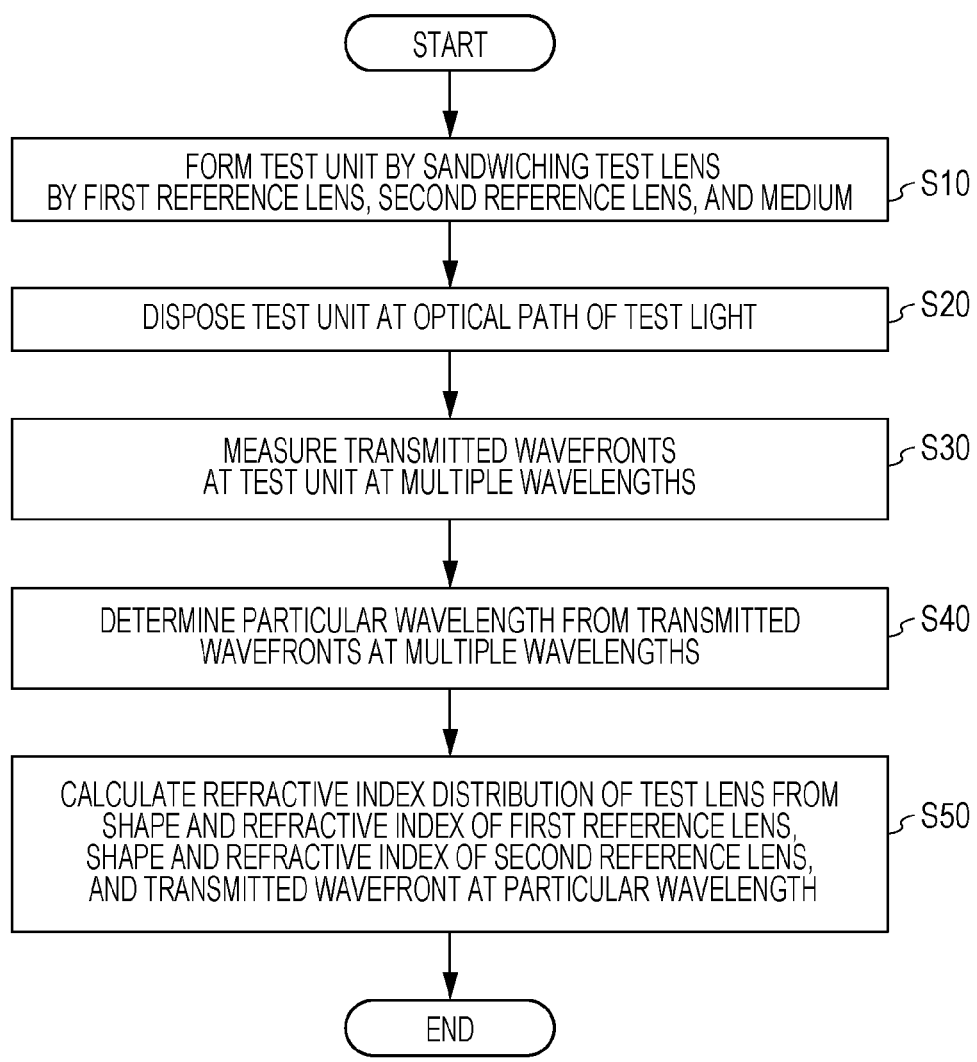
FIG. 2 is a flowchart illustrating a procedure for calculating the refractive index distribution of a test lens according to the first embodiment.

FIG. 2 is a flowchart illustrating a procedure for calculating the refractive index distribution of the test lens 60. In the first embodiment, first, the test lens 60 is sandwiched by the first reference lens 120, the second reference lens 125, and the medium 71 to form the test unit 200 (S10).

Figure 3:
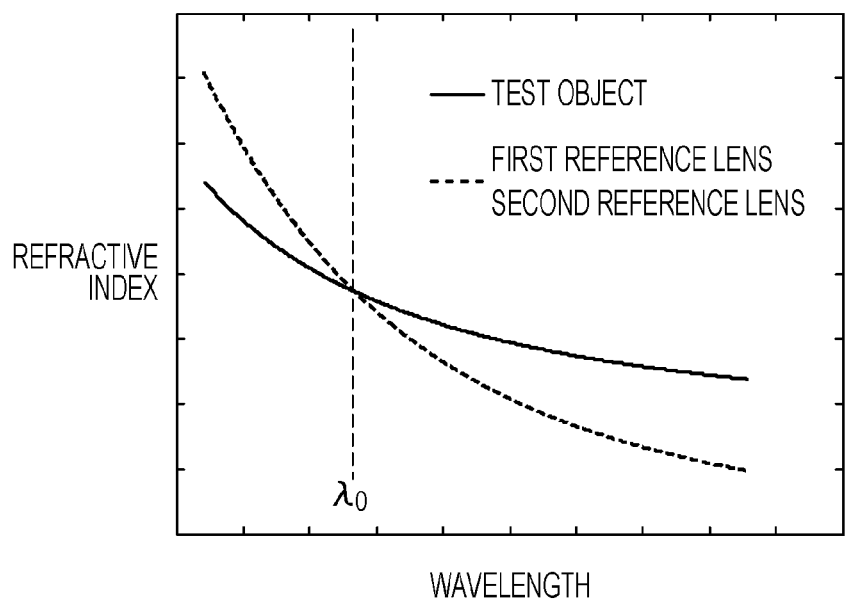
FIG. 3 illustrates a dispersion curve of the refractive index of a test lens and a dispersion curve of the refractive indices of first and second reference lenses.

As shown in FIG. 3, the refractive index dispersion of the first reference lens 120, which is the same as the refractive index dispersion of the second reference lens 125, differs from the refractive index dispersion of the test lens 60 (test object). At a particular wavelength $\lambda_0$, the refractive indices of the first reference lens 120 and the second reference lens 125 are equal to the refractive index of the test lens 60. In general, the absolute value of the refractive index of a molded lens varies greatly depending upon the molding conditions. If the refractive index dispersions of the first reference lens 120 and the second reference lens 125 are the same as the refractive index dispersion of the test lens 60, the slopes of the two curves shown in FIG. 3 are substantially the same. Therefore, an intersection of the two curves (at the particular wavelength $\lambda_0$) may not exist. Consequently, in the first embodiment, it is desirable that the materials of the first reference lens 120 and the second reference lens 125 differ from the material of the test lens 60.

Next, the test unit 200 is disposed in an optical path of test light (S20). While controlling wavelengths at the monochromator 20, transmitted wavefronts of the test unit 200 at a plurality of wavelengths are measured (S30). Then, the particular wavelength $\lambda_0$ is determined from the transmitted wavefronts of the test unit 200 at the plurality of wavelengths (S40).

The particular wavelength $\lambda_0$ refers to a wavelength where the refractive index at a particular point in the interior of the test lens 60 and the refractive indices of the first and second reference lenses are the same. At the wavelength where the refractive indices are the same, the difference between the transmitted wavefronts at the front and the back of the test unit 200 is small. Therefore, the particular wavelength $\lambda_0$ can be determined from the sizes of the transmitted wavefronts. In particular, the transmitted wavefronts become large at a portion where the slope of the second surface is steep with respect to the first surface of the test lens 60. Therefore, when this portion is used, the particular wavelength $\lambda_0$ can be determined. For example, a transmitted wavefront near a cut edge of the test lens is suitable for determining the particular wavelength $\lambda_0$.

The particular wavelength $\lambda_0$ may be determined from interference fringes instead of from transmitted wavefronts. When the particular wavelength $\lambda_0$ is determined from interference fringes, while controlling wavelengths at the monochromator 20, interference fringes at a plurality of wavelengths are measured, and the wavelength where the interference fringes become smallest (=the particular wavelength $\lambda_0$) is determined.

Transmitted wavefronts are measured by using a fringe scan method in which the mirror 105 is driven. A transmitted wavefront W $(\lambda_0, x, y)$ of the test unit at the particular wavelength $\lambda_0$ is expressed by Equation (1):

$$W(\lambda_0,x,y)=n_0(\lambda_0)L_A(x,y)+n^{medium}(\lambda_0)L_B(x,y)+n^{sample}(\lambda_0,x,y)L(x,y)+n^{medium}(\lambda_0)L_C(x,y)+n_0(\lambda_0)L_D(x,y)-n_0(\lambda_0)L+C \quad (1)$$

Figure 4A:
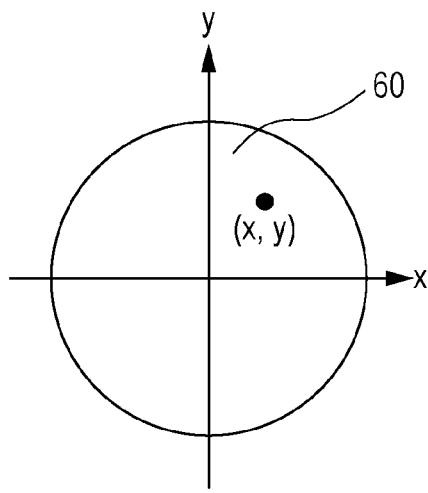
FIG. 4A illustrates a coordinate system defined at the test lens.
Figure 4B:
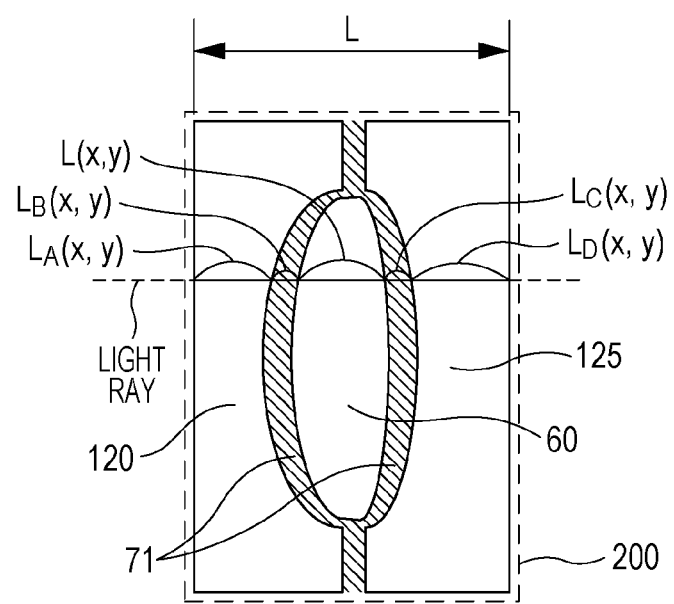
FIG. 4B illustrates an optical path of a light ray and parameters of the lens unit in the measuring apparatus, according to the first embodiment.

$L_A(x, y)$, $L_B(x, y)$, $L(x, y)$, $L_C(x, y)$, and $L_D(x, y)$ are geometric distances between the respective surfaces of optical components along a light ray shown in FIG. 4B. The light ray in FIG. 4B refers to a light ray that passes through a point (x, y) in the interior of the test lens 60 shown in FIG. 4A. FIG. 4B is drawn by ignoring any deflection of the light ray by refraction at each surface.

L(x, y) represents the thickness of the test lens 60. $L_A$(x, y) represents the thickness of the first reference lens 120. $L_D$(x, y) represents the thickness of the second reference lens 125. $L_A$(x, y) and $L_D$(x, y) are measured by, for example, a surface profiler, and are defined as known quantities. $L_B$(x, y) and $L_C$(x, y) represent small gaps that occur when the shape of the second surface of the first reference lens 120 and the shape of the first surface of the test lens 60 differ slightly and when the shape of the second surface of the test lens 60 and the shape of the first surface of the second reference lens 125 differ slightly. These gaps are filled with the medium 71.

$n^{sample}(\lambda_0, x, y)$ represents the refractive index of the test lens 60 at the particular wavelength $\lambda_0$. $n_0(\lambda_0)$ represents the refractive index of each of the first reference lens 120 and the second reference lens 125 at the particular wavelength $\lambda_0$, and each refractive index is a known value. In the first embodiment, it is assumed that the refractive index of the first reference lens 120 and the refractive index of the second reference lens 125 are the same, and are homogeneous in the interiors of the lenses.

$n^{medium}(\lambda_0)$ represents the refractive index of the medium 71 at the particular wavelength $\lambda_0$.

L is the sum of $L_A$(x, y), $L_B$(x, y) L(x, y), $L_C$(x, y), and $L_D$(x, y). A relational expression is expressed by Equation (2). The right side of Equation (2) is known, and is substantially equal to the design value of the thickness of the test lens 60:

$$L_B(x,y)+L(x,y)+L_C(x,y)=L-(L_A(x,y)+L_D(x,y)) \quad (2)$$

C is an arbitrary constant. In the interferometer, a wavefront piston, which means a constant component of an equiphase surface (DC component), cannot be measured. Therefore, a wavefront that has been measured by the interferometer includes an uncertain quantity C of the constant component. $n_0(\lambda_0)L$ in Equation (1) is a constant term and is part of the constant term C. However, it is separated from the constant term C in order to use in the following calculation. Equation (1) can be calculated into Equation (3) by using Equation (2):

$$[n^{sample}(\lambda_0,x,y)-n_0(\lambda_0)][(L-(L_A(x,y)+L_D(x,y))]=W(\lambda_0,x,y)+(n^{sample}(\lambda_0,x,y)-n^{medium}(\lambda_0))(L_B(x,y)+L_C(x,y))-C \quad (3)$$

If both sides of Equation (3) are divided by $L-(L_A(x, y)+L_D(x, y))$, the refractive index distribution expressed by Equation (4) is calculated. The second term and the third term on the right side in Equation (4) correspond to a calculation error of the refractive index distribution:

$$n^{sample}(\lambda_0, x, y) - n_0(\lambda_0) = \quad (4)$$
$$\frac{W(\lambda_0, x, y)}{L-(L_A(x,y)+L_D(x,y))} + (n^{sample}(\lambda_0, x, y) - n^{medium}(\lambda_0))$$
$$\frac{L_B(x,y)+L_C(x,y)}{L-(L_A(x,y)+L_D(x,y))} - \frac{C}{L-(L_A(x,y)+L_D(x,y))}$$

The third term in Equation (4) is a component that results from the uncertain constant term C that cannot be measured by the interferometer. Therefore, a large error depending upon the value of C may occur in the refractive index distribution. Therefore, the following correction calculation is performed.

At a particular point $(x_0, y_0)$ in the interior of the test lens 60, the refractive index of the test lens 60 is equal to the refractive index $n_0(\lambda_0)$ of each of the first and second reference lenses ($n^{sample}(\lambda_0, x_0, y_0) = n_0(\lambda_0)$). Here, at the point ($x_0, y_0$), Equation (3) is represented as Equation (5). If, after subtracting Equation (5) from Equation (3), this result is divided by $L-(L_A(x, y)+L_D(x, y))$, the refractive index distribution that excludes the error caused by the value of C is obtained by Equation (6):

$$0 = W(\lambda_0, x_0, y_0) + \qquad (5)$$
$$(n^{sample}(\lambda_0, x_0, y_0) - n^{medium}(\lambda_0))(L_B(x_0, y_0) + L_C(x_0, y_0)) - C$$

$$n^{sample}(\lambda_0, x, y) - n_0(\lambda_0) = \qquad (6)$$
$$\frac{W(\lambda_0, x, y) - W(\lambda_0, x_0, y_0)}{L - (L_A(x, y) + L_D(x, y))} + (n^{sample}(\lambda_0, x, y) - n^{medium}(\lambda_0))$$
$$\frac{L_B(x, y) - L_B(x_0, y_0) + L_C(x, y) - L_C(x_0, y_0)}{L - (L_A(x, y) + L_D(x, y))}$$

If the difference between the refractive index of the test lens 60 and the refractive index of each of the first and second reference lenses is small, and if the refractive index distribution of the test lens 60 is close to zero, it is safe to assume that the constant term C is zero. However, in general, since the refractive index of the test lens 60 changes during molding process and a refractive index distribution occurs, if it is assumed that C=0, the precision is reduced. In the first embodiment, a transmitted wavefront is measured at the particular wavelength $\lambda_0$ where the refractive index of the test lens 60 and the refractive index of each of the first and second reference lenses are equal to each other, and the error caused by the constant term C is cancelled by the calculations using Equations (5) and (6). Therefore, the precision is high.

If the shape of the first surface of the test lens 60 and the shape of the second surface of the first reference lens 120, and the shape of the second surface of the test lens 60 and the shape of the first surface of the second reference lens 125 match within the range on the order of manufacturing errors of the surface shape of the test lens, the second term on the right side of Equation (6) can be negligible. That is, an approximation Equation (7) is obtained:

$$(n^{sample}(\lambda_0, x, y) - n^{medium}(\lambda_0)) \qquad (7)$$
$$\frac{L_B(x, y) - L_B(x_0, y_0) + L_C(x, y) - L_C(x_0, y_0)}{L - (L_A(x, y) + L_D(x, y))} \sim 0$$

Accordingly, at step S50 of FIG. 2, a refractive index distribution GI ($\lambda_0$, x, y) of the test lens 60 at the particular wavelength is calculated by Equation (8). The denominator on the right side of Equation (8) (that is, $L-(L_A(x, y)+L_D(x,y))$) is substantially equal to the design value of the thickness of the test lens 60. Therefore, the design value of the thickness of the test lens 60 may be used in place of $L-(L_A(x, y)+L_D(x,y))$:

$$GI(\lambda_0, x, y) = n^{sample}(\lambda_0, x, y) - n_0(\lambda_0) = \frac{W(\lambda_0, x, y) - W(\lambda_0, x_0, y_0)}{L - (L_A(x, y) + L_D(x, y))} \qquad (8)$$

In the measuring method according to the first embodiment, an error in the calculation of the refractive index distribution that occurs due to an error in the shape of the test lens 60 (deviation from the design value of the shape) and an error in the refractive index of the test lens 60 (deviation from the design value of the refractive index) is corrected by using the shapes and the refractive indices of the reference lenses. Therefore, it is possible to nondestructively measure the refractive index distribution of an optical element with high precision.

In the measuring method according to the first embodiment, the refractive index distribution of the test lens 60 is measured without using a medium (matching liquid) having a refractive index that is substantially equal to the refractive index of the test lens 60. Therefore, the refractive index distribution of an optical element with high refractive indices ($n_d$~1.8 or greater) for which no effective matching liquid is available can also be calculated with high precision.

In the first embodiment, as shown in FIG. 1, the refractive index distribution of the test lens 60 is measured with test light vertically incident upon the test lens 60. However, as shown in FIGS. 5A to 5D, it is possible to measure the refractive index distribution of the test lens 60 even with test light obliquely incident upon the test lens 60. By measuring the refractive index distribution of the test lens 60 with test light obliquely incident upon the test lens 60, it is possible to calculate a refractive index distribution in an optical axis direction of the test lens 60. The term "optical axis direction" refers to a direction from a first surface vertex to a second surface vertex of the test lens 60.

First, at a plurality of dispositions in which tilts of the test unit 200 differ with respect to test light, transmitted wavefronts of the test unit 200 are measured. The tilt angle of the test unit 200 with respect to the test light is adjusted by controlling the amount of rotation of the rotating stage 140 by the computer 90.

The refractive index distributions of the test lens 60 are calculated at the plurality of dispositions. The refractive index distributions are projected values of the three-dimensional refractive index distribution of the test lens 60 in transmission directions of the test light. The projected values of the refractive index distribution of the test lens based on dispositions in which the test light is obliquely incident upon the test lens 60 includes information about the refractive index distribution in the optical axis direction of the test lens 60 in accordance with the different tilt angles. If the projected value of the refractive index distribution is calculated at the plurality of dispositions, it is possible to extract the information about the refractive index distribution in the optical axis direction of the test lens 60.

Figure 5A:
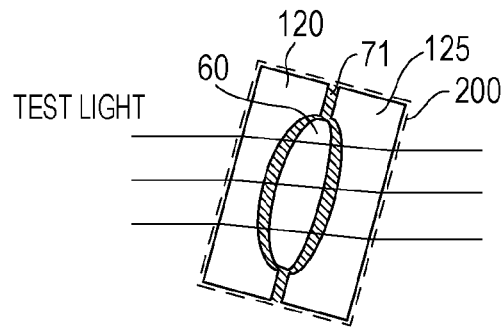
FIGS. 5A to 5D illustrate a plurality of dispositions in which a test unit is tilted with respect to a beam of test light according to the first embodiment.
Figure 5B:
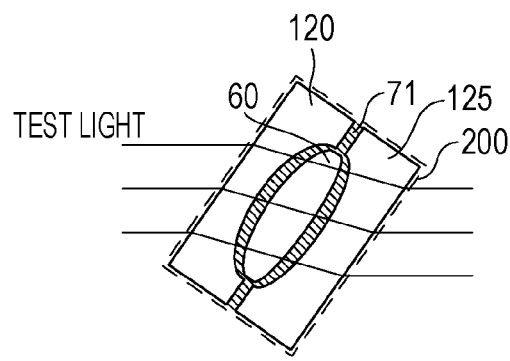

FIGS. 5A and 5B each illustrate directions of propagation of light rays when the test unit 200 is tilted with respect to the test light. As the tilt angle of the test unit 200 is increased, the refracting angle at a surface of the test unit 200 is increased. As the refracting angle is increased, the shift amount of the test light that passes through the test unit 200 with respect to the incident test light is increased. Due to the influence of the refraction, the incident angle of the test light with respect to the test lens 60 is smaller than the tilt angle of the test unit 200, which is not desirable. Specifically, when the incident angle is small, enough information about the refractive index distribution in the optical axis direction of the test lens 60 cannot be acquired.

Figure 5C:
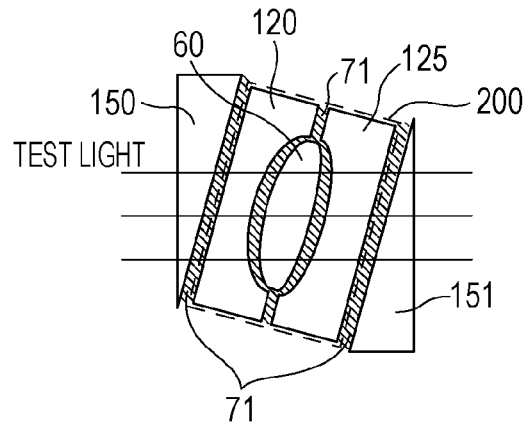
Figure 5D:
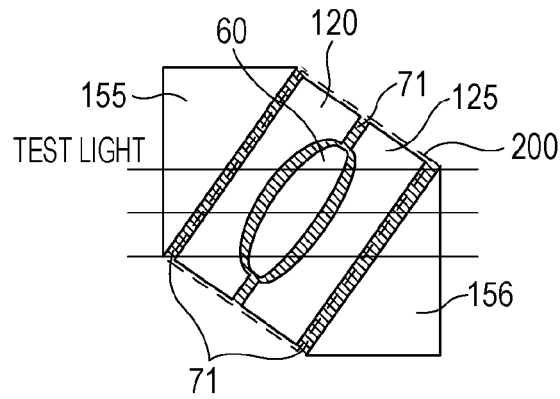

FIGS. 5C and 5D illustrate a method for solving the undesirability of small incidence angle. In FIG. 5C, the influence of the refraction is reduced by inserting prisms 150 and 151 in front of and in back of the test unit 200. However, the prisms 150 and 151 should have vertex angles that are the same as the tilt angle of the test unit 200 with respect to the test light beam. In FIG. 5D, the influence of the refraction is reduced by inserting prisms 155 and 156 having vertex angles that are the same as the tilt angle of the test unit 200 in front of and in back of the test unit 200.

The prisms 150, 151, 155, and 156 are made of the same material as the first and second reference lenses. A gap between the prism 150 and the test unit 200, a gap between the prism 151 and the test unit 200, a gap between the prism 155 and the test unit 200, and a gap between the prism 156 and the test unit 200 are each filled with a medium 71 for reducing the influence of the refraction in these gaps.

As shown in FIGS. 5C and 5D, by using prisms having vertex angles that are the same as the tilt angle of the test unit 200, a projected value of the refractive index distribution at an incident angle that is the same as the tilt angle of the test unit 200 can be acquired.

An optical path length distribution (=refractive index distribution×L(x, y)) may be used in place of the refractive index distribution as a physical quantity that indicates optical characteristics of a molded lens. Therefore, the refractive index distribution measuring method (refractive index distribution measuring apparatus) according to the present invention means an optical path length distribution measuring method (optical path length distribution measuring apparatus).

In the first embodiment, wavelength scanning is performed by using a combination of a light source that emits light having a plurality of wavelengths and a monochromator. Although a supercontinuum light source is described as the light source that emits light having a plurality of wavelengths in the first embodiment, an optical frequency comb, a super luminescent diode (SLD), a short pulse laser, or a halogen lamp may also be used instead.

Instead of a combination of a light source that emits light having a plurality of wavelengths and a monochromator, a wavelength-swept light source or a multi-line laser that discretely emits a plurality of wavelengths may be used. The number of light sources that emit light having a plurality of wavelengths is not limited to one. A plurality of light sources may be combined. In the first embodiment, the light source or light sources only need to be light sources that emit light having two or more different wavelengths.

In the first embodiment, a Mach-Zehnder interferometer is used as the interference optical system. A Twyman-Green interferometer or a Fizeau interferometer may also be used instead.

Second Embodiment

In a second embodiment, a refractive index distribution measuring method when the difference between the shape of the second surface of a first reference lens 120 and the shape of the first surface of a test lens 60 and the difference between the shape of the second surface of the test lens 60 and the shape of the first surface of a second reference lens 125 are greater than those in the first embodiment is described. In the second embodiment, the differences between the surface shapes (shape component) are removed by using transmitted wavefronts of two different wavelengths.

Figure 6:
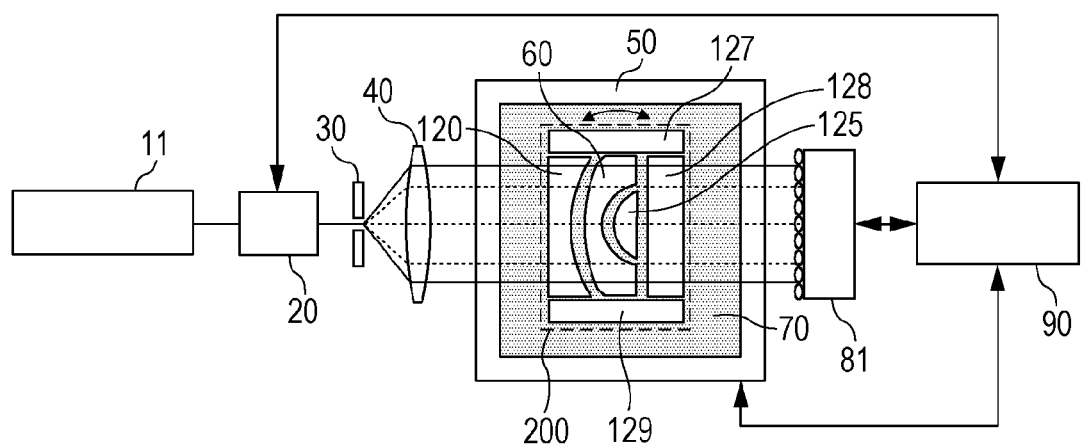
FIG. 6 is a schematic view of a structure of a refractive index distribution measuring apparatus according to a second embodiment of the present invention.

FIG. 6 is a schematic view of a structure of a refractive index distribution measuring apparatus according to the second embodiment of the present invention. In the second embodiment, a transmitted wavefront is measured by using a Shack-Hartman sensor 81 instead of using the interference optical system used in the first embodiment. A light source 11 is a multi-line gas laser (such as an argon laser or a krypton laser). A test lens 60 has a negative refractive power. In FIG. 6, components similar to those of the first embodiment are assigned with the respective same reference numerals and thus description thereof is omitted.

A test unit 200 is disposed in a medium 70 with which a container 50 is filled. As shown in FIG. 6, the test unit 200 according to the second embodiment includes the first reference lens 120, the test lens 60, the second reference lens 125, the medium 70, and auxiliary glasses 127, 128, and 129. The test unit 200 has a parallelepiped (or circular cylindrical) shape as a whole. The first and second surfaces of the test lens 60 are aspherical surfaces. The second surface of the first reference lens 120 is a spherical surface having a shape that is similar to the aspherical shape of the first surface of the test lens 60. The first surface of the second reference lens 125 is a spherical surface having a shape that is similar to the aspherical shape of the second surface of the test lens 60.

In the second embodiment, a refractive index $n^{sample}(\lambda, a, b)$ near a cut edge of the test lens 60 is known. It is possible to measure the refractive index of the test lens 60 by a minimum angle-of-deviation method by, for example, processing a portion near the cut edge of the test lens 60 into the form of a prism. The first reference lens 120, the second reference lens 125, and the auxiliary glasses 127, 128, and 129 are all made of the same material. The surface shapes and refractive indices $n_0(\lambda)$ are all known quantities.

Light from the light source 11 is spectrally separated by a monochromator 20, passes through a pinhole 30 and becomes divergent light, and passes through a collimator lens 40 and becomes parallel light. The parallel light passes through the test unit 200 disposed in the medium 70 in the container 50, and is detected by the Shack-Hartman sensor 81. A signal detected by the Shack-Hartman sensor 81 is sent to a computer 90. A thermometer (not shown) is disposed in the container 50. The refractive index of the medium 70 is calculated by the computer 90 by using the temperature of the medium 70 measured by the thermometer and a temperature coefficient of the refractive index of the medium 70.

A method for calculating the refractive index distribution of the test lens 60 according to the second embodiment is hereunder described. In the second embodiment, first, the test unit 200 is formed by sandwiching the test lens 60 by the first reference lens 120, the second reference lens 125, the medium 70, and the auxiliary glasses 127, 128, and 129. Then, the test unit 200 is disposed in an optical path of the parallel light in the container 50.

A first transmitted wavefront $W(\lambda_1, x, y)$ of the test unit 200 at a first wavelength $\lambda_1$ (such as $\lambda_1$=457 nm) and a second transmitted wavefront $W(\lambda_2, x, y)$ of the test unit 200 at a second wavelength $\lambda_2$ (such as $\lambda_2$=514 nm) are measured. A transmitted wavefront $W(\lambda, x, y)$ at a wavelength $\lambda$ is expressed by Equation (9). Further, it is possible to modify Equation (9) to Equation (11) by using Equation (2) and an approximation Equation (10). Equation (11) is expressed by Equation (12) at coordinates (a, b). Equation (13) is obtained by subtracting Equation (12) from Equation (11) and removing a constant term C. The meanings of the symbols in the Equations are the same as those in the first embodiment:

$$W(\lambda,x,y) = n_0(\lambda)L_A(x,y) + n^{medium}(\lambda)L_B(x,y) + n^{sample}(\lambda,x,y)L(x,y) + n^{medium}(\lambda)L_C(x,y) + n_0(\lambda)L_D(x,y) - n(\lambda,a,b)L + C = (n^{sample}(\lambda,x,y) - n^{sample}(\lambda,a,b))(L_B(x,y) + L(x,y) + L_C(x,y)) - n^{sample}(\lambda,x,y) - n^{medium}(\lambda))(L_B(x,y) + L_C(x,y)) + (n_0(\lambda) - n^{sample}(\lambda,a,b))(L_A(x,y) + L_D(x,y)) + C \quad (9)$$

$$(n^{sample}(\lambda,a,b) - n^{sample}(\lambda,x,y))(L_B(x,y) + L_C(x,y)) \sim 0 \quad (10)$$

$$W(\lambda,x,y) = (n^{sample}(\lambda,x,y) - n^{sample}(\lambda,a,b))[L - (L_A(x,y) + L_D(x,y))] - (n^{sample}(\lambda,a,b) - n^{medium}(\lambda))(L_B(x,y) + L_C(x,y)) + (n_0(\lambda) - n^{sample}(\lambda,a,b))(L_A(x,y) + L_D(x,y)) + C \quad (11)$$

$$W(\lambda,a,b) = (n^{sample}(\lambda,a,b) - n^{medium}(\lambda))(L_B(a,b) + L_C(a,b)) + (n_0(\lambda) - n^{sample}(\lambda,a,b))(L_A(a,b) + L_D(a,b)) + C \quad (12)$$

$$W(\lambda,x,y)-W(\lambda,a,b)=(n^{sample}(\lambda,x,y)-n^{sample}(\lambda,a,b))[L-L_A(x,y)+L_D(x,y))]-(n^{sample}(\lambda,a,b)-n^{medium}(\lambda)(L_B(x,y)-L_B(a,b)+L_C(x,y)-L_C(a,b))+(n_0(\lambda)-n^{sample}(\lambda,a,b))(L_A(x,y)-L_A(a,b)+L_D(x,y)-L_D(a,b)) \quad (13)$$

By using the shape and the refractive index of the first reference lens 120, the shape and the refractive index of the second reference lens 125, the transmitted wavefront of the test unit 200 at the first wavelength, and the transmitted wavefront of the test unit 200 at the second wavelength, it is possible to remove the difference between the surface shape of the test lens 60 and the surface shape of each of the first and second reference lenses (shape component), that is, it is possible to remove $L_B(x, y)-L_B(0, 0)+L_C(x, y)-L_C(0, 0)$.

A refractive index distribution GI ($\lambda_1$, x, y) of the test lens 60 at the first wavelength is calculated by Equation (15) by using an approximation Equation (14). A refractive index distribution GI ($\lambda_2$, x, y) of the test lens 60 at the second wavelength is expressed by Equation (16) by using Equations (14) and (15):

$$\frac{n^{sample}(\lambda_2, x, y) - n^{sample}(\lambda_1, x, y)}{n^{sample}(\lambda_1, x, y) - 1} \approx \frac{n^{sample}(\lambda_2, a, b) - n^{sample}(\lambda_1, a, b)}{n^{sample}(\lambda_1, a, b) - 1} \quad (14)$$

$$\therefore n^{sample}(\lambda_2, x, y) - n^{sample}(\lambda_2, a, b) = \frac{n^{sample}(\lambda_2, a, b) - 1}{n^{sample}(\lambda_1, a, b) - 1}(n^{sample}(\lambda_1, x, y) - n^{sample}(\lambda_1, a, b))$$

$$GI(\lambda_1, x, y) = n^{sample}(\lambda_1, x, y) - n^{sample}(\lambda_1, a, b) = \quad (15)$$

$$\frac{A(\lambda_1)\begin{bmatrix} W(\lambda_2, x, y) - \\ W(\lambda_2, a, b) \end{bmatrix} - A(\lambda_2)[W(\lambda_1, x, y) - W(\lambda_1, a, b)]}{\left(\frac{n^{sample}(\lambda_2, a, b) - 1}{n^{sample}(\lambda_1, a, b) - 1}A(\lambda_1) - A(\lambda_2)\right)} -$$

$$[L - (L_A(x, y) + L_D(x, y))]$$

$$\frac{A(\lambda_1)(n_0(\lambda_2) - n^{sample}(\lambda_2, a, b)) - \frac{A(\lambda_2)(n_0(\lambda_1) - n^{sample}(\lambda_1, a, b))}{\frac{n^{sample}(\lambda_2, a, b) - 1}{n^{sample}(\lambda_1, a, b) - 1}A(\lambda_1) - A(\lambda_2)}}{L_A(x, y) - L_A(a, b) + L_D(x, y) - L_D(a, b)} \times$$

$$\frac{L_A(x, y) - L_A(a, b) + L_D(x, y) - L_D(a, b)}{L - (L_A(x, y) + L_D(x, y))}$$

$$A(\lambda) = n^{sample}(\lambda, a, b) - n^{medium}(\lambda)$$

$$GI(\lambda_2, x, y) = \frac{n^{sample}(\lambda_2, a, b) - 1}{n^{sample}(\lambda_1, a, b) - 1}GI(\lambda_1, x, y) \quad (16)$$

In the second embodiment, when the difference between the surface shape of the test lens and the surface shape of the first reference lens and the difference between the surface shape of the test lens and the surface shape of the second reference lens are large, the refractive index distribution is calculated by removing the differences between the surface shapes (shape component) by using the transmitted wavefronts of two different wavelengths. In removing the shape component, two types of media having different refractive indices may be used instead of two different wavelengths. If the test unit 200 is formed from two types of media having different refractive indices, and the transmitted wavefronts of the test unit 200 are measured, it is possible to calculate the refractive index distribution by removing the shape component. A method therefor is as follows.

A first test unit is formed by sandwiching a test lens 60 by a first reference lens 120, a second reference lens 125, a first medium having a first refractive index $n_1^{medium}$ ($\lambda$) and auxiliary glasses 127, 128, and 129. A first transmitted wavefront of the first test unit is measured. A first transmitted wavefront $W_1$ ($\lambda$, x, y) of the first test unit is expressed by Equation (17):

$$W_1(\lambda,x,y)=(n^{sample}(\lambda,x,y)-n^{sample}(\lambda,a,b))[L-(L_A(x,y)+L_D(x,y))]-(n^{sample}(\lambda,a,b)-n_1^{medium}(\lambda))(L_B(x,y)+L_C(x,y))+(n_0(\lambda)-n^{sample}(\lambda,a,b))(L_A(x,y)+L_D(x,y))+C \quad (17)$$

A second test unit is formed by sandwiching the test lens 60 by the first reference lens 120, the second reference lens 125, a second medium having a second refractive index $n_2^{medium}$ ($\lambda$) that differs from the first refractive index $n_1^{medium}$ ($\lambda$), and the auxiliary glasses 127, 128, and 129. A second transmitted wavefront of the second test unit is measured. A second transmitted wavefront $W_2$ ($\lambda$, x, y) of the second test unit is expressed by Equation (18):

$$W_2(\lambda,x,y)=(n^{sample}(\lambda,x,y)-n^{sample}(\lambda,a,b))[L-(L_A(x,y)+L_D(x,y))]-(n^{sample}(\lambda,a,b)-n_2^{medium}(\lambda))(L_B(x,y)+L_C(x,y))+(n_0(\lambda)-n^{sample}(\lambda,a,b))(L_A(x,y)+L_D(x,y))+C \quad (18)$$

Lastly, by using the shape and the refractive index of the first reference lens 120, the shape and the refractive index of the second reference lens 125, the first transmitted wavefront, and the second transmitted wavefront, the refractive index distribution is calculated by removing the shape component of the test lens 60. It is possible to remove the constant term C by a method similar to that using Equations (12) and (13). A refractive index distribution GI ($\lambda$, x, y) of the test lens 60 is expressed by Equation (19):

$$GI(\lambda, x, y) = n^{sample}(\lambda, x, y) - n^{sample}(\lambda, a, b) = \quad (19)$$

$$\frac{B_1(\lambda)\begin{bmatrix} W_2(\lambda, x, y) - \\ W_2(\lambda, a, b) \end{bmatrix} - B_2(\lambda)[W_1(\lambda, x, y) - W_1(\lambda, a, b)]}{(B_1(\lambda) - B_2(\lambda))[L - (L_A(x, y) + L_D(x, y))]} -$$

$$\frac{(n_0(\lambda) - n^{sample}(\lambda, a, b))}{L - (L_A(x, y) + L_D(x, y))} \cdot (L_A(x, y) - L_A(a, b) + L_D(x, y) - L_D(a, b))$$

$$B_k(\lambda) = n^{sample}(\lambda, a, b) - n_k^{medium}(\lambda) \; (k = 1, 2)$$

It is possible to reduce the influence of the difference between the surface shape of the test lens 60 and the surface shape of the first reference lens and the difference between the surface shape of the test lens 60 and the surface shape of the second reference lens by, instead of using two different wavelengths or two types of media, using a transmitted wavefront of a reference test unit in which a reference test lens having a particular refractive index distribution is sandwiched by a first reference lens and a second reference lens.

Here, it is assumed that the refractive index distribution of the reference test lens is a refractive sample index distribution having a uniform refractive index n ($\lambda$, a, b). As the shape of the reference test lens, a design value of the test lens 60 is used. A transmitted wavefront $W_{sim}$($\lambda$, x, y) of the reference test unit that is formed by sandwiching the reference test lens by the first reference lens and the second reference lens is expressed by Equation (20), where C' is an arbitrary constant:

$$W_{sim}(\lambda,x,y)=-(n^{sample}(\lambda,a,b)-n^{medium}(\lambda))(L_B(x,y)+L_C(x,y))-(n^{sample}(\lambda,a,b)-n^{medium}(\lambda))(\delta L_B(x,y)+\delta L_C(x,y))+(n_0(\lambda)-n^{sample}(\lambda,a,b))(L_A(x,y)+L_D(x,y))+C' \quad (20)$$

$\delta L_B(x, y)$ represents the difference between the shape of the first surface of the test lens 60 and the shape of the first surface of the reference test lens, and $\delta L_C(x, y)$ represents the difference between the shape of the second surface of the test lens 60 and the shape of the second surface of the reference test lens. When the transmitted wavefront $W_{sim}$ ($\lambda$, x, y) of the reference test unit is used, it is possible to reduce the influence of the difference between the surface shape of the test lens 60 and the surface shape of the first reference lens and the difference between the surface shape of the test lens 60 and the surface shape of the second reference lens (that is, the influence of the second term on the right in Equation (11)).

The difference between the transmitted wavefront ($\lambda$, x, y) at of the test unit 200 (Equation (11)) and the transmitted wavefront $W_{sim}$ ($\lambda$, x, y) of the reference test unit (Equation (20)) is expressed by Equation (21):

$$W(\lambda,x,y) - W_{sim}(\lambda,x,y) = (n^{sample}(\lambda,x,y) - n^{sample}(\lambda,a,b))$$
$$[L - (L_A(x,y) + L_D(x,y))] + (n^{sample}(\lambda,a,b) - n^{medium}(\lambda))(\delta L_B(x,y) + \delta L_C(x,y)) + C - C' \quad (21)$$

$\delta L_B$ (x, y) and $\delta L_C$(x, y) are small values on the order of manufacturing errors of the test lens 60. Therefore, the approximation Equation (22) is obtained. When a constant term C−C' is removed from Equation (21) by a method similar to that using Equations (12) and (13), and when the approximation Equation (22) is used, the refractive index distribution GI ($\lambda$, x, y) of the test lens 60 is expressed by Equation (23):

$$\frac{(n^{sample}(\lambda, a, b) - n^{medium}(\lambda))(\delta L_B(x, y) + \delta L_C(x, y))}{L - (L_A(x, y) + L_D(x, y))} \sim 0 \quad (22)$$

$$GI(\lambda, x, y) = n^{sample}(\lambda, x, y) - n^{sample}(\lambda, a, b) =$$
$$\frac{[W(\lambda, x, y) - W(\lambda, a, b)] - [W_{sim}(\lambda, x, y) - W_{sim}(\lambda, a, b)]}{L - (L_A(x, y) + L_D(x, y))} \quad (23)$$

In the second embodiment, the Shack-Hartman sensor 81 is used for measuring a transmitted wavefront of the test unit 200. A shearing interferometer, such as a Talbot interferometer, may be used instead of the Shack-Hartman sensor.

Although, in the second embodiment, wavelengths are controlled by using the monochromator 20, a wavelength selective filter may be used instead of the monochromator.

In the second embodiment, a light source that emits a plurality of wavelengths (a multi-line gas laser) is used. However, when a system that uses two types of media or a system that uses a reference test lens is used, a light source having a single wavelength (such as an HeNe laser) may be used.

The results of refractive index distributions measured by using the apparatuses and methods described in the first and second embodiments may be fed back to a method for manufacturing an optical element, such as a molded lens.

Figure 7:
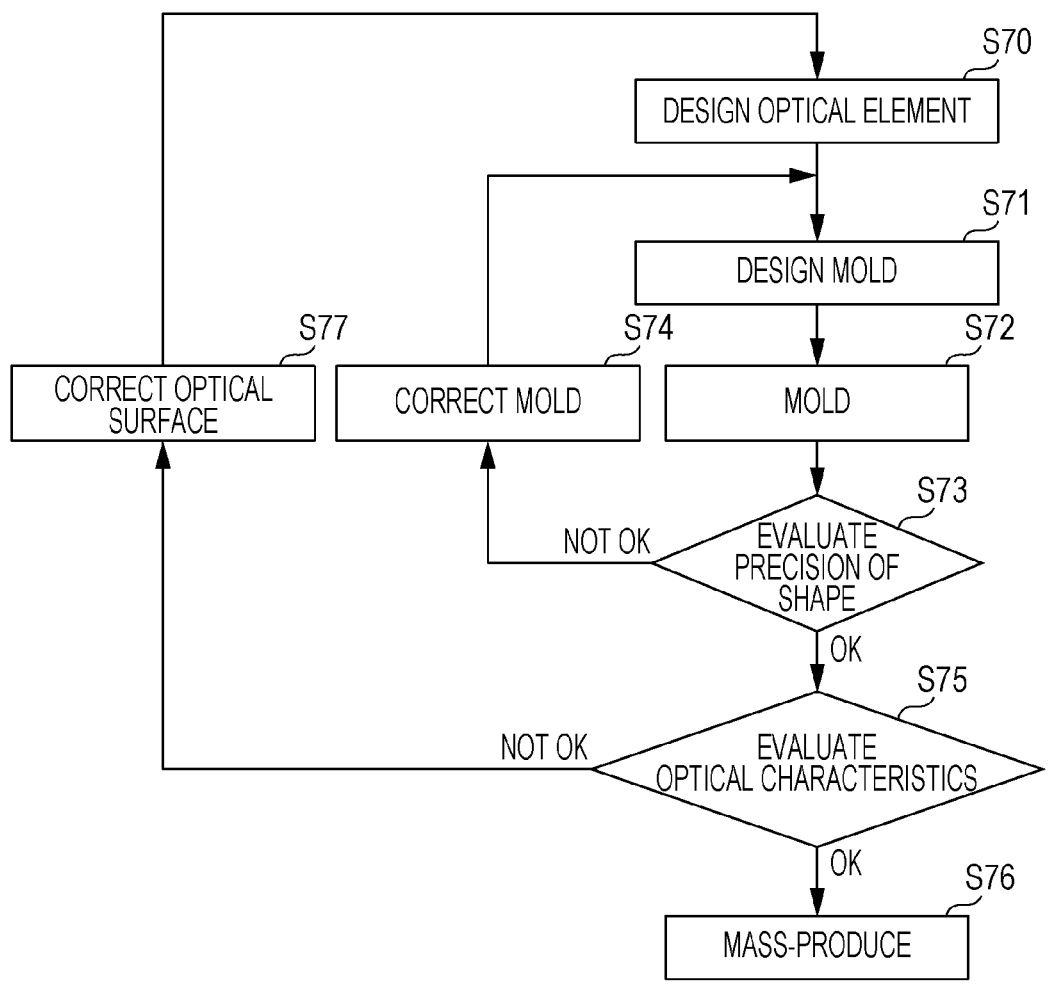
FIG. 7 illustrates process steps of an optical element manufacturing method according to the present invention.

FIG. 7 illustrates steps for manufacturing an optical element by molding.

The optical element is manufactured by performing the step of designing the optical element (S70), the step of designing the mold (S71), and a step of molding the optical element by using the designed mold (S72). The precision of the shape of the molded optical element is evaluated at an evaluating step S73. If the shape is not precise enough (not OK at S73), the mold is corrected to re-mold the optical element (S74). If precision of the shape is acceptable (OK at S73), optical characteristics of the optical element are evaluated at S75. By including the refractive index distribution measuring method according to the present invention in the step of evaluating the optical characteristics (S75), it is possible to mass-produce (S76) high-precision optical elements formed by molding by using a glass material having a high refractive index as a base material. When the optical characteristics of the optical element do not match desired design parameters (not OK at S75), the optical element whose optical surface has been corrected at S77 is re-designed by repeating the flow process of FIG. 7.

The embodiments described above are merely typical embodiments. In carrying out the invention, various modifications and changes may be made on each of the embodiments.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-248475, filed Dec. 8, 2014, and Japanese Patent Application No. 2015-190070, filed Sep. 28, 2015, which are hereby incorporated by reference herein in their entirety.

What is claimed is:

1. A refractive index distribution measuring method comprising:
    measuring a wavefront of light transmitted through a test unit that is formed by sandwiching a test lens between a first reference lens whose shape and refractive index are known, a second reference lens whose shape and refractive index are known, and a medium; and
    calculating a refractive index distribution of the test lens from the shape and the refractive index of the first reference lens, the shape and the refractive index of the second reference lens, and the measured wavefront of the test unit.

2. The refractive index distribution measuring method according to claim 1, wherein the first reference lens and the second reference lens are formed of a same material, and the refractive index of the first reference lens and the refractive index of the second reference lens are equal to a refractive index of the test lens at a particular wavelength.

3. The refractive index distribution measuring method according to claim 2, wherein
    transmitted wavefronts of the test unit are measured at a plurality of wavelengths,
    the particular wavelength is determined from the transmitted wavefronts of the test unit at the plurality of wavelengths, and
    the refractive index distribution of the test lens is calculated by using a measured wavefront at the particular wavelength.

4. The refractive index distribution measuring method according to claim 1, wherein
    transmitted wavefronts of the test unit are measured at a plurality of dispositions in which the test unit is tilted with respect to test light, and
    a refractive index distribution in an optical axis direction of the test lens is calculated by using the measured wavefronts of the test unit at the plurality of dispositions.

5. The refractive index distribution measuring method according to claim 1, wherein a transmitted wavefront of the test unit at a first wavelength and a transmitted wavefront of the test unit at a second wavelength that differs from the first wavelength are measured, and by using the shape and the refractive index of the first reference lens, the shape and the refractive index of the second reference lens, the measured wavefront of the test unit at the first wavelength, and the measured wavefront of the test unit at the second wavelength, the refractive index distribution of the test lens is calculated by removing a shape component of the test lens.

6. The refractive index distribution measuring method according to claim 1, wherein, in the measuring step, a transmitted wavefront of a first test unit that is formed by sandwiching the test lens between the first reference lens, the second reference lens, and a first medium having a first refractive index is measured, a transmitted wavefront of a second test unit that is formed by sandwiching the test lens between the first reference lens, the second reference lens, and a second medium having a second refractive index that differs from the first refractive index is measured, and wherein, in the calculating step, by using the shape and the refractive index of the first reference lens, the shape and the refractive index of the second reference lens, the measured wavefront of the first test unit, and the measured wavefront of the second test unit, the refractive index distribution of the test lens is calculated by removing a shape component of the test lens.

7. The refractive index distribution measuring method according to claim 1, further comprising:

measuring a wavefront of light transmitted through a reference test unit that is formed by sandwiching a reference test lens having a particular refractive index distribution by the first reference lens and the second reference lens, wherein, in the calculating step, by using the shape and the refractive index of the first reference lens, the shape and the refractive index of the second reference lens, the measured wavefront of the test unit, and the measured wavefront of the reference test unit, the refractive index distribution of the test lens is calculated.

8. An optical element manufacturing method comprising the steps of:

molding an optical element; and evaluating optical characteristics of the molded optical element, wherein the step of evaluating optical characteristics of the optical element includes the step of measuring a wavefront of light transmitted through a test unit that is formed by sandwiching the optical element between a first reference lens whose shape and refractive index are known, a second reference lens whose shape and refractive index are known, and a medium, and the step of calculating a refractive index distribution of the optical element from the shape and the refractive index of the first reference lens, the shape and the refractive index of the second reference lens, and the measured wavefront of the test unit.

9. A refractive index distribution measuring apparatus comprising:

a measuring unit configured to measure a wavefront of light transmitted through a test unit that is formed by sandwiching a test lens between a first reference lens whose shape and refractive index are known, a second reference lens whose shape and refractive index are known, and a medium; and a calculating unit configured to calculate a refractive index distribution of the test lens from the shape and the refractive index of the first reference lens, the shape and the refractive index of the second reference lens, and the measured wavefront of the test unit.

10. The refractive index distribution measuring apparatus according to claim 9, wherein a surface of the first reference lens and a surface of the second reference lens that are on opposite sides of the test lens are planar surfaces.

11. The refractive index distribution measuring apparatus according to claim 9, wherein the measuring unit includes a Mach-Zehnder interferometer.

12. The refractive index distribution measuring apparatus according to claim 9, wherein the measuring unit includes a Shack-Hartman sensor.

13. The refractive index distribution measuring apparatus according to claim 9, wherein the measuring unit includes a shearing interferometer.

* * * * *